US00PP09415P

United States Patent [19]

Delbard

[11] Patent Number: Plant 9,415

[45] Date of Patent: Jan. 2, 1996

[54] HYBRID TEA ROSE PLANT NAMED 'DELROUMO'

[75] Inventor: Georges Delbard, Commentry, France

[73] Assignee: Société Civile Agricole, Pépiniéres et Roseraies Georges Delbard, Commentry, France

[21] Appl. No.: 334,115

[22] Filed: Nov. 4, 1994

[51] Int. Cl.[6] ..... A01H 5/00

[52] U.S. Cl. ..... Plt./20

[58] Field of Search ..... Plt./20, 21

[56] References Cited

U.S. PATENT DOCUMENTS

P.P. 4,037 4/1977 Paolino ..... Plt./20

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which abundantly forms attractive double flowers which are medium red in coloration. Such flowers are long lasting and comprise petals which detach cleanly. The plant exhibits an upright to bushy growth habit, forms very vigorous vegetation, and is well suited for greenhouse forcing for cut flowr production. Additionally, the plant is resistant to diseases when grown under greenhouse conditions.

1 Drawing Sheet

SUMMARY OF THE INVENTION

The new variety of Hybrid Tea rose plant was created by artificial pollination wherein two parents possessing red blossoms were crossed which previously had been studied in the hope that they would contribute the desired characteristics. The female parent (i.e., the seed parent) of the new variety was the Delricos variety. The male parent (i.e., the pollen parent) was the Red Success (also known as 'Meirodium' and the subject of U.S. Plant Pat. No. 4,037) variety. The parentage of the new variety can be summarized as follows:

DELRICOS×RED SUCCESS

The seeds resulting from the above pollination were sown and 270 small plantlets were obtained which were physically and biologically different from each other. Selective study resulted in the identification of a single plant of the new variety.

It was found through careful study that the new variety of the present invention can be characterized by the following combination of characteristics:

(a) from a physical point of view it forms green mature wood, assumes an upright to bushy growth habit, and forms attractive long-lasting medium red double flowers having consistent petals which detach cleanly, and (b) from the biological point of view it forms very vigorous vegetation, produces flowers in abundance, exhibits the ability readily to be forced, and is resistant to diseases when grown under greenhouse conditions.

The new variety well meets the needs of the horticultural industry and is particularly well suited for growing in the greenhouse for the production of attractive long-lasting medium red cut flowers.

The new variety can be readily distinguished from other varieties in view of the combination of characteristics described herein. It exhibits long and relatively straight stems, rigid and substantially straight peduncles, an excellent ability to be forced under greenhouse conditions, and a long vase life for its distinctive medium red blossoms.

The new variety has been found to undergo asexual propagation and can be readily reproduced by conventional routes, such as budding (i.e., eye grafting). This asexual reproduction as performed in France has demonstrated that the characteristics of the new variety are strictly transmissible from one generation to another and are firmly fixed.

The new variety has been named the Delroumo variety.

BRIEF DESCRIPTION OF THE PHOTOGRAPH

The accompanying photograph shows as nearly true as it is reasonably possible to make the same in a color illustration of this character typical specimens of the plant parts of the new variety. The rose plants of the new variety were grown under glass Hyères (Var), France.

FIG. 1 — illustrates a specimen of a flowering stem;

FIG. 2 — illustrates a specimen of a main branch;

FIG. 3 — illustrates a specimen of a floral bud at the opening of the sepals;

FIG. 4 — illustrates a specimen of a floral bud at the opening of the petals;

FIGS. 5 and 6 — illustrates a specimen of a flower in the course of opening;

FIG. 7 — illustrates a specimen of an open flower — plan view — reverse;

FIG. 8 — illustrates a specimen of an open flower — plan view — obverse;

FIGS. 9 and 10 — illustrates a specimen of a fully open flower — plan view — obverse;

FIG. 11 — illustrates a specimen of a floral receptacle showing the arrangement of the stamens and pistils;

FIG. 12 — illustrates a specimen of a floral receptacle showing the arrangement of the pistils (sepals and stamens removed);

FIG. 13 — illustrates a specimen of a single leaf — plan view — upper surface;

FIG. 14 — illustrates a specimen of a leaf with three leaflets — plan view — upper surface;

FIG. 15 — illustrates a specimen of a leaf with five leaflets — plan view — upper surface (above), and lower surface (below);

FIG. 16 — illustrates a specimen of a leaf with seven leaflets — plan view — upper surface; and FIG. 17 — illustrates a specimen of a young shoot.

DETAILED DESCRIPTION

Figures 1, 2, 5, 6, 11, 12:
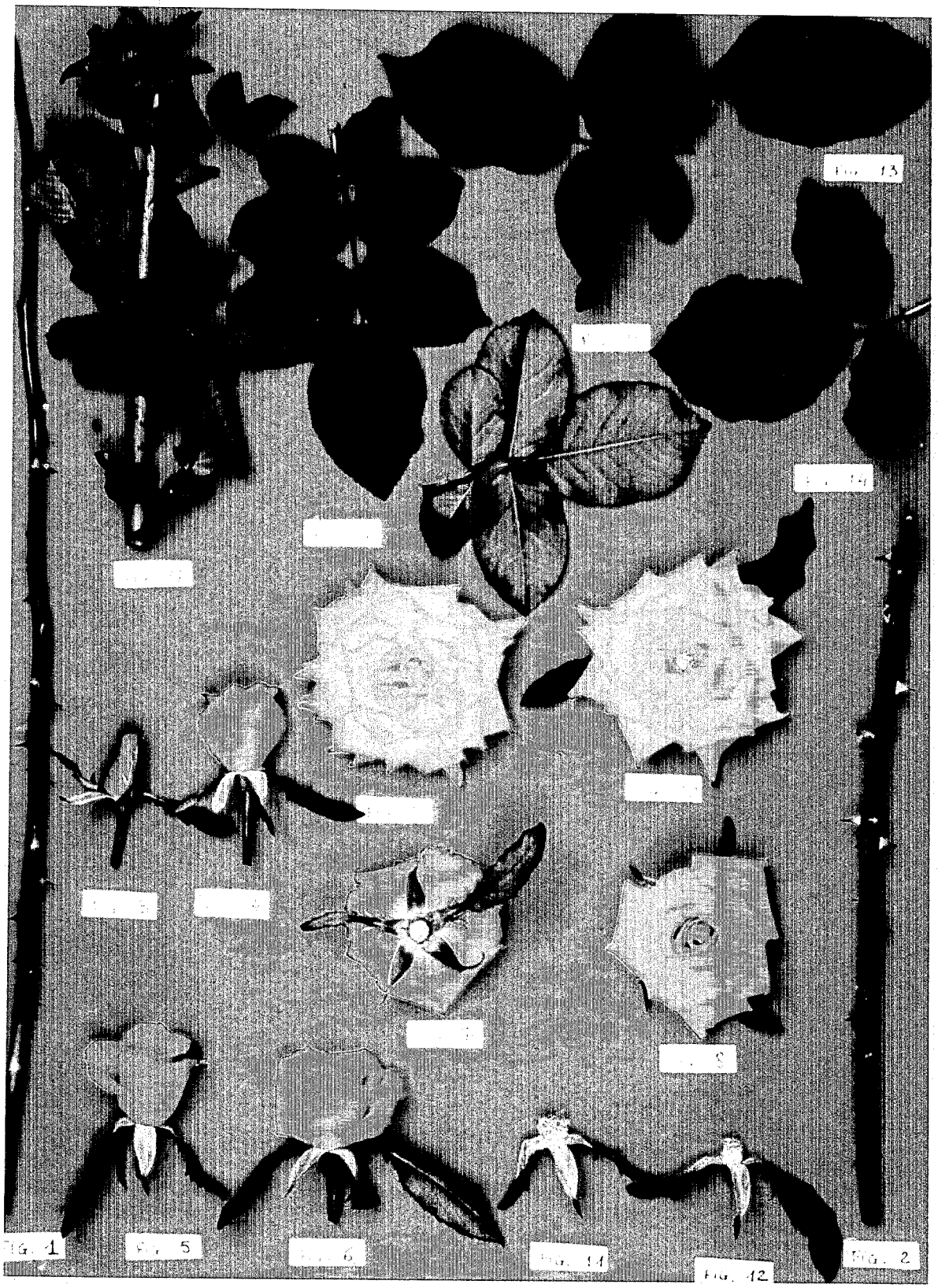

The chart used in the identification of the colors is that of The Royal Horticultural Society (R.H.S. Colour Chart). The description is based on the observation of plants grown under glass at Hyères (Var), France. The coloration in common terms sometimes also is provided.

Class: Hybrid Tea.

Plant:

*Height.*—Plants which were pruned at a height of 1 m. produce floral stems having a length of: Means: 80 to 90 cm. Range: 50 to 120 cm.

*Habit.*—Upright to bushy.

Branches:

*Color.*—Young shoots: when approximately 20 cm. long, exhibit a bronze coloration; Greyed-Purple Group R.H.S. 183 B becoming rapidly green: Yellow-Green Group R.H.S. 146 B. Floral stems: Yellow-Green Group R.H.S. 146 B. Mature Wood: Yellow-Green Group R.H.S. 146 A.

*Thorns.*—Configuration: concave on upper surface and deep concave on lower surface. Quantity: For a stem 80 cm long: There are no thorns on the basal 30 cm. On the next 20 cm of the stem, thorns roughly 10 mm long are present about every 2.5 cm. On the last 30 cm of the stem, there are many thorns of approximately 1 to 5 mm in length, and thorns about 10 mm long about every 1.5 cm. Length: approximately 10 mm on average on floral stems and approximately 10 mm. on average on mature wood, and commonly range from about 1 to 13 mm. in length in each instance. Color: when present on a shoot approximately 20 cm. long are Yellow-Green Group R.H.S. 144 B; when present on floral stems are Yellow-Green Group R.H.S. 144 B during summer time and Havana brown; Greyed-Orange Group R.H.S. 165 A–165 B during winter time in green-house; and when present on mature wood are havana brown; Greyed-Orange Group R.H.S. 165 A–165 B.

*Leaves.*—Number: normal amount for the class. Size: very large. Stipules: adnate, large, normal for the class.

*Leaflets.*—Number: commonly 1, 3, 5, rarely 7; average: 5. Size: long. Shape: as illustrated, and in cross section are flat. Serration: single but irregular. General appearance: texture very weak on floral stem, medium glossiness in summer, strong glossiness in winter. Petiole color on young shoot: Green: Yellow-Green Group R.H.S. 146 C on upper surface and green: Yellow-Green Group R.H.S. 146 B on under surface. Petiole color on floral stem: Green: Yellow-Green Group R.H.S. 146 C on upper surface and green: Yellow-Green Group R.H.S. 146B on under surface. Petiole color on mature wood: Green: Yellow-Green Group R.H.S. 146 C on upper surface and green: Yellow-Green Group R.H.S. 146 B on under surface. Petiole: Upper surface: from 0 to 5 very small hooked prickles of 1 to 2 mm Under surface: grooved without glandular edges. Petiole length of terminal leaflet: Approximately 15 to 28 mm, approximately 25 mm on average, and a standard deviation of 2 mm. Terminal leaflet length: Approximately 65 to 110 mm, approximately 80 mm on average, and a standard deviation of 10 mm. Terminal leaflet width: Approximately 45 to 70 mm, approximately 60 mm on average, and a standard deviation of 5 mm. Terminal leaflet shape at base: Obtuse to rounded. Leaflet color of young shoot: Bronze: Greyed-Purple Group R.H.S. 187 A–187 B on upper surface and reddish; Greyed-Purple Group R.H.S. 183 B on under surface. Leaflet color on floral stem: Green: Yellow-Green Group R.H.S. 147 A on upper surface and green: Yellow-Green Group R.H.S. 147 B on the under surface. Leaflet color of mature wood: Green: Yellow-Green Group R.H.S. 147 A on upper surface and green: Yellow-Green Group R.H.S. 147 B on under surface.

Inflorescence:

*Number of flowers.*—Generally one per stem when grown under forced greenhouse conditions.

*Peduncle.*—Some small hairs are present and is light green: Yellow-Green Group R.H.S 144 A in coloration. Average length: 130 mm — from 110 to 140 mm.

*Sepals.*—Configuration: very strong for one sepal, medium for the two other and very weak for the two remaining. Color: Yellow-Green Group R.H.S. 147 C on the base and R.H.S. 147 A on the top on upper surface, and Yellow-Green Group R.H.S. 147 B on under surface. Length: average 45 mm but one sepal sometimes goes to 100 mm.

*Buds.*—Before calyx breaks: Size: 28 to 35 mm, average 33 mm. Shape: ovate. As calyx breaks: The color is Red Group R.H.S. 46 B–46 C to R.H.S. 46 A (in winter). As first petals open: Size: big, average 55 mm. Color upper surface: Red Group R.H.S. 52 A. Color under surface: Red Group R.H.S. 46 B–46 C.

*Flower.*—Time: medium to begin flowering. Shape: double. Diameter: medium to large, approximately 110 to 145 mm, and approximately 122 mm on average with a standard deviation of 10 mm. Petal number: commonly approximately 25 to 35, and an average of approximately 30. Petal form: View from above: irregulary rounded. Side view of upper part: flattened convex. Side view of lower part: flat. Petal size (second row from outside): the length is approximately 54 to 65 mm with a mean of approximately 60 mm, and a standard deviation of 3 mm; and the with is approximately 55 to 73 mm with a mean of approximately 62 mm, and a standard deviation of 5 mm. Petal shape: the first row of petals commonly exhibit a very broad obovate configuration, the undulation of the petal margin is medium, and the reflexing of the margin is medium. Petal texture: soft but not thin. Petal color: this description was made on a rose grown in greenhouse at Hyères in the South of France in Jun. 1994 and which was opened for 3 days. Petal color (middle zone): Red: Red Group R.H.S. 52 A. Petal color (marginal zone): Red: Red Group R.H.S. 46 B–46 C. Petal spot at base: very small in size, on the inner side Yellow Group R.H.S. 4 D nearly white, and on the outer side Yellow Group R.H.S. 4 D nearly white. Stamens: approximately 72 in number and are somewhat regularly arranged around the pistils. Filaments: medium to long in length and Red-Purple Group R.H.S. 63 A in coloration. Anthers: medium in size, all open at approximately the same time, and the immature coloration is Orange Group R.H.S. 24 B–24 C. Pollen: very small amount in quantity and yellow in coloration. Pistils: approximately 86 in number. Styles: medium to long in length Red Group R.H.S. 46 B–46 C near the stigmas, and pale yellow: Yellow Group R.H.S. 13 D at the base in coloration. Stigmas: Yellow-Orange Group R.H.S. 23 C in coloration, and generally are present at about the same level as the anthers, but a few anthers may be higher. Hips: no hips. Seeds: none. Petal drop: petals detach cleanly. Fragrance: very weak. Lasting quality: good: 7 days average.

Development:

*Vegetation.*—Very vigorous.

*Blooming.*—Very abundant and almost continuous.

*Aptitute to forcing.*—Excellent.

*Resistance to diseases.*—Good under greenhouse conditions, and is a little sensitive to powdery mildew.

This variety is a greenhouse Hybrid Tea, very vigorous, with big and long stems (average 80–90 cm), large foliage with a big bud, medium red, good vase life and good production for this type of rose.

I claim:

1. A new and distinct variety of Hybrid Tea rose plant characterized by the following combination of characteristics:

(a) from a physical point of view it forms green mature wood, assumes an upright to bushy growth habit, and forms attractive long-lasting medium red double flowers having consistent petals which detach cleanly, and (b) from the biological point of view forms very vigorous vegetation, produces flowers in abundance, exhibits the ability readily to be forced, and is very resistant to diseases when grown under greenhouse conditions;

substantially as herein shown and described.

* * * * *